US009808289B2

(12) United States Patent
Ross et al.

(10) Patent No.: US 9,808,289 B2
(45) Date of Patent: Nov. 7, 2017

(54) EXTERNAL FIXATOR RING

(71) Applicant: TEXAS SCOTTISH RITE HOSPITAL FOR CHILDREN, Dallas, TX (US)

(72) Inventors: John D. Ross, Ovilla, TX (US); Mikhail L. Samchukov, Coppell, TX (US); Alexander M. Cherkashin, Flower Mound, TX (US); John G. Birch, Dallas, TX (US)

(73) Assignee: TEXAS SCOTTISH RITE HOSPITAL FOR CHILDREN, Dallas, TX (US)

( * ) Notice: Subject to any disclaimer, the term of this patent is extended or adjusted under 35 U.S.C. 154(b) by 0 days.

(21) Appl. No.: 15/082,704

(22) Filed: Mar. 28, 2016

(65) Prior Publication Data
US 2016/0206349 A1 Jul. 21, 2016

Related U.S. Application Data

(63) Continuation of application No. 12/864,534, filed as application No. PCT/US2009/033258 on Feb. 5, 2009, now Pat. No. 9,295,493.
(Continued)

(51) Int. Cl.
*A61B 17/62* (2006.01)
*A61B 17/56* (2006.01)

(52) U.S. Cl.
CPC ........ *A61B 17/62* (2013.01); *A61B 2017/564* (2013.01); *Y10T 29/49963* (2015.01)

(58) Field of Classification Search
CPC ...................................................... A61B 17/62
(Continued)

(56) References Cited

U.S. PATENT DOCUMENTS 2,238,870 A   4/1941  Haynes
2,346,346 A   4/1944  Anderson
(Continued)

FOREIGN PATENT DOCUMENTS

CA   2633944 A1   7/2007
DE   3802743 A1   8/1989
(Continued)

OTHER PUBLICATIONS

International Search Report and Written Opinion, PCT/US2013/064067, dated Jan. 31, 2014, 7 pages.
(Continued)

*Primary Examiner* — Nicholas Plionis
(74) *Attorney, Agent, or Firm* — Baker & McKenzie LLP

(57) ABSTRACT

The present disclosure includes an external fixator ring that includes a central opening, inner and outer ring surfaces and upper and lower ring surfaces. In some embodiments, one or more apertures are defined in the inner or outer surface for receiving securing devices. The apertures in the inner or outer surface are adapted to provide rigid attachment for connection struts while allowing for a range of motion between the interconnected rings. In some other embodiments, the external fixator ring further comprises angled flanges extending radially from the inner or outer surface. The angle flanges each include a mounting surface, apertures are defined in the mounting surface of the angle flanges for receiving securing devices.

26 Claims, 9 Drawing Sheets

Related U.S. Application Data

(60) Provisional application No. 61/026,396, filed on Feb. 5, 2008.

(58) Field of Classification Search
USPC .................................................... 606/53–59
See application file for complete search history.

(56) References Cited

U.S. PATENT DOCUMENTS

| | | |
|---|---|---|
| 4,308,863 A | 1/1982 | Fischer |
| 4,365,624 A | 12/1982 | Jaquet |
| 4,621,627 A | 11/1986 | DeBastiani et al. |
| 4,768,524 A | 9/1988 | Hardy |
| 4,889,111 A | 12/1989 | Ben-Dov |
| 4,973,331 A | 11/1990 | Pursley et al. |
| 4,988,244 A | 1/1991 | Sheldon et al. |
| 5,019,077 A | 5/1991 | De Bastiani et al. |
| 5,095,919 A | 3/1992 | Monticelli et al. |
| 5,156,605 A | 10/1992 | Pursley et al. |
| 5,180,380 A | 1/1993 | Pursley et al. |
| 5,458,599 A | 10/1995 | Adobbati |
| 5,533,418 A | 7/1996 | Wu et al. |
| 5,630,814 A | 5/1997 | Ross, Jr. et al. |
| 5,702,389 A | 12/1997 | Taylor et al. |
| 5,728,095 A | 3/1998 | Taylor et al. |
| 5,776,132 A | 7/1998 | Blyakher |
| 5,797,908 A | 8/1998 | Meyers et al. |
| 5,863,292 A | 1/1999 | Tosic |
| 5,885,283 A | 3/1999 | Gittleman |
| 5,891,143 A | 4/1999 | Taylor et al. |
| 5,928,230 A | 7/1999 | Tosic |
| 5,971,984 A | 10/1999 | Taylor et al. |
| 6,030,386 A | 2/2000 | Taylor et al. |
| 7,282,052 B2 | 10/2007 | Mullaney |
| RE40,914 E | 9/2009 | Taylor et al. |
| 8,029,505 B2 | 10/2011 | Hearn et al. |
| 8,202,273 B2 | 6/2012 | Karidis |
| 8,257,353 B2 | 9/2012 | Wong |
| 8,296,094 B2 | 10/2012 | Harrison et al. |
| 8,333,766 B2 | 12/2012 | Edelhauser et al. |
| 8,366,710 B2 | 2/2013 | Hirata et al. |
| 8,377,060 B2 | 2/2013 | Vasta et al. |
| 8,388,619 B2 | 3/2013 | Mullaney |
| 2002/0010465 A1 | 1/2002 | Koo et al. |
| 2003/0149378 A1 | 8/2003 | Peabody et al. |
| 2003/0191466 A1 | 10/2003 | Austin et al. |
| 2003/0199856 A1 | 10/2003 | Hill et al. |
| 2003/0212398 A1 | 11/2003 | Jackson |
| 2004/0073211 A1 | 4/2004 | Austin et al. |
| 2004/0097922 A1 | 5/2004 | Mullaney |
| 2004/0116926 A1 | 6/2004 | Venturini et al. |
| 2004/0204711 A1* | 10/2004 | Jackson ............ A61B 17/7035 606/308 |
| 2005/0192572 A1 | 9/2005 | Abdelgany et al. |
| 2005/0215997 A1 | 9/2005 | Austin et al. |
| 2005/0234457 A1 | 10/2005 | James et al. |
| 2006/0052782 A1 | 3/2006 | Morgan et al. |
| 2006/0207118 A1 | 9/2006 | Kim |
| 2006/0235389 A1 | 10/2006 | Albert et al. |
| 2007/0055234 A1 | 3/2007 | McGrath et al. |
| 2007/0055254 A1 | 3/2007 | Ihde |
| 2007/0083087 A1 | 4/2007 | Carda |
| 2007/0085496 A1 | 4/2007 | Philipp et al. |
| 2007/0225704 A1 | 9/2007 | Ziran et al. |
| 2007/0233134 A1 | 10/2007 | Bastian et al. |
| 2008/0021451 A1 | 1/2008 | Coull et al. |
| 2009/0036890 A1 | 2/2009 | Karidis |
| 2009/0036892 A1 | 2/2009 | Karidis et al. |
| 2009/0177198 A1* | 7/2009 | Theodoros ............ A61B 17/66 606/56 |
| 2010/0087819 A1 | 4/2010 | Mullaney |
| 2010/0262160 A1 | 10/2010 | Boyden et al. |
| 2010/0262239 A1 | 10/2010 | Boyden et al. |
| 2010/0305568 A1 | 12/2010 | Ross et al. |
| 2010/0312243 A1 | 12/2010 | Ross et al. |
| 2010/0331840 A1 | 12/2010 | Ross et al. |
| 2011/0004199 A1 | 1/2011 | Ross et al. |
| 2011/0118738 A1 | 5/2011 | Vasta et al. |
| 2011/0166572 A1 | 7/2011 | Ihde |
| 2011/0313418 A1 | 12/2011 | Nikonovas |
| 2011/0313419 A1 | 12/2011 | Mullaney |
| 2012/0041439 A1 | 2/2012 | Singh et al. |
| 2012/0130384 A1 | 5/2012 | Henderson |
| 2012/0303028 A1 | 11/2012 | Wong |
| 2012/0303029 A1 | 11/2012 | Vasta et al. |
| 2013/0018374 A1 | 1/2013 | Edelhauser et al. |

FOREIGN PATENT DOCUMENTS

| | | | |
|---|---|---|---|
| DE | 9316164 U1 | 7/1994 | |
| DE | 4421223 A1 | 12/1995 | |
| DE | 102007026404 A1 | 12/2008 | |
| EP | 0029298 A1 | 5/1981 | |
| EP | 1239784 B1 | 4/2006 | |
| EP | 1916952 B1 | 12/2009 | |
| EP | 2134515 B1 | 7/2010 | |
| EP | 2417923 A1 | 2/2012 | |
| GB | 421788 | 12/1934 | |
| GB | 2229096 A | 9/1990 | |
| IT | 1259768 B | 3/1996 | |
| JP | S52-003290 | 8/1978 | |
| JP | S63-500499 | 2/1988 | |
| JP | H02180254 A | 7/1990 | |
| JP | H10290807 A | 11/1998 | |
| JP | 2003508108 A | 3/2003 | |
| JP | 2003508150 A | 3/2003 | |
| JP | 2005-137586 | 6/2005 | |
| RU | WO 2007075114 A1 * | 7/2007 | ............ A61B 17/62 |
| WO | 9222268 A1 | 12/1992 | |
| WO | 9626678 A1 | 9/1996 | |
| WO | 9730650 A1 | 8/1997 | |
| WO | 9812975 A2 | 4/1998 | |
| WO | 9815231 A1 | 4/1998 | |
| WO | 9920193 A1 | 4/1999 | |
| WO | 9947060 A1 | 9/1999 | |
| WO | 9948414 A2 | 9/1999 | |
| WO | 0003647 A1 | 1/2000 | |
| WO | 0115611 A1 | 3/2001 | |
| WO | 0122892 A1 | 4/2001 | |
| WO | 03086211 A1 | 10/2003 | |
| WO | 03086212 A2 | 10/2003 | |
| WO | 03086213 A2 | 10/2003 | |
| WO | 2004026103 A2 | 4/2004 | |
| WO | 2007002180 A2 | 1/2007 | |
| WO | 2007060507 A2 | 5/2007 | |
| WO | 2007139031 A1 | 12/2007 | |
| WO | 2008002992 A1 | 1/2008 | |
| WO | 2008134624 A1 | 11/2008 | |
| WO | 2009018349 A2 | 2/2009 | |
| WO | 2009018398 A2 | 2/2009 | |
| WO | 2009100247 A1 | 8/2009 | |
| WO | 2009100459 A1 | 8/2009 | |
| WO | 2009102904 A1 | 8/2009 | |
| WO | 2009105479 A1 | 8/2009 | |
| WO | 2010042619 A1 | 4/2010 | |
| WO | 2010104567 A1 | 9/2010 | |
| WO | 2010120367 A1 | 10/2010 | |
| WO | 2011017321 A2 | 2/2011 | |
| WO | 2011060264 A1 | 5/2011 | |
| WO | 2011060266 A1 | 5/2011 | |
| WO | 2011106507 A1 | 9/2011 | |
| WO | 2011146703 A1 | 11/2011 | |
| WO | 2011163406 A2 | 12/2011 | |

OTHER PUBLICATIONS

International Search Report and Written Opinion, PCT/RU2013/000203, dated Jan. 29, 2014, 23 pages.

Canero, C., et al., "Predictive (Un)distortion Model and 3-D Reconstruction by Biplane Snakes, IEEE Transactions on Medical Imaging," vol. 21, No. 9, (Sep. 2002), 14 pages.

Ghanem, R.N., et al., "Heart-Surface Reconstruction and ECG Electrodes Localization Using Fluoroscopy, Epipolar Geometry and

(56) References Cited

OTHER PUBLICATIONS

Stereovision: Application to Noninvasive Imaging of Cardiac Electrical Activity," IEEE Transactions on Medical Imaging, vol. 22, No. 10, (Oct. 2003), 12 pages.
Li, Y., et al., "Distortion Correction and Geometric Calibration for X-Ray Angiography System," IEEE Transactions on Nuclear Science, vol. 56, No. 3, (Jun. 2009), 12 pages.
Selby, B.P., et al., "Patient positioning with X-ray detector self-calibration for image guided therapy," Australas Phys. Eng. Sci. Med., vol. 34, (2011), 10 pages.
Yang, J., et al., "Novel Approach for 3-D Reconstruction of Coronary Arteries From Two Uncalibrated Angiographic Images," IEEE Transactions on Image Processing, vol. 18, No. 7, (Jul. 2009), 10 pages.
Zheng, G., et al., "A 2D/3D correspondence building method for reconstruction of a patient-specific 3D bone surface model using point distribution models and calibrated X-ray images," Medical Image Analysis, vol. 13, (2009), 17 pages.
Extended European Search Report, EP Application No. 09707791.1-1654 / PCT/US2009/033258, dated Nov. 21, 2013, 6 pages.
Extended European Search Report, EP Application No. 09708841.3-1654 / 2240085; PCT/US2009/033603, dated Dec. 2, 2013, 5 pages.
Japanese Office Action, dated Nov. 26, 2013, JP Application No. 2010-545284, 4 pages.
Extended European Search Report, EP Application No. 09710983.9-1654 / 2249721; PCT/US2009/033975, dated Apr. 4, 2014, 7 pages.
Japanese Office Action, JP Application No. 2010-545284, dated Mar. 5, 2013, 6 pages.
International Search Report and Written Opinion, PCT/US2009/033258, dated Mar. 19, 2009, 9 pages.
International Search Report, PCT/US2009/034413, dated Apr. 15, 2009, 1 page.
International Preliminary Report on Patentability, PCT/US2009/034413, dated Aug. 24, 2010, 7 pages.
Extended European Search Report, EP Application No. 09712412.7-1526; PCT/US2009/034413, dated Dec. 3, 2012, 10 pages.
International Search Report, PCT/US2010/056541, dated Jan. 12, 2011, 1 page.
International Preliminary Report on Patentability, PCT/US2010/056541, dated May 15, 2012, 7 pages.
International Preliminary Report on Patentability, PCT/US2010/056539, dated May 15, 2012, 9 pages.
International Search Report, PCT/US2010/056539, dated Jan. 18, 2011, 2 pages.
Steffen Schumann, et al., "Calibration of X-ray radiographs and its feasible application for 2D/3D reconstruction of the proximal femur," (2008), 12 pages.
Jetzki, S., et al., "Fluoroscopy-Based 3-D Reconstruction of Femoral Bone Cement: A New Approach for Revision Total Hip Replacement," (2005), 12 pages.
Guoyan Zheng, et al., "3-D reconstruction of a surface model of the proximal femur from digital biplanar radiographs," (2008), 4 pages.
Laporte, S., et al., "A biplanar reconstruction method based on 2D and 3D contours: application to the distal femur," (2003), 6 pages.
Japanese Office Action, JP Application No. 2010-546960, dated Mar. 12, 2013, 4 pages.
Japanese Office Action, JP Application No. 2010-546904, dated Mar. 12, 2013, 6 pages.
Japanese Office Action, JP Application No. 2010-546098, dated Mar. 5, 2013, 11 pages.
International Preliminary Report on Patentability, PCT/RU2010/000452, dated Feb. 26, 2013, 9 pages.
Japanese Office Action, JP Application No. 2010-546904, dated Oct. 29, 2013, 4 pages.

* cited by examiner

EXTERNAL FIXATOR RING

CROSS-REFERENCE TO RELATED APPLICATION(S)

This application is a continuation of patent application Ser. No. 12/864,534, filed on Jul. 26, 2010, which application is a national phase filing under section 371 of PCT/US2009/033258, filed Feb. 5, 2009, which application claims the benefit of and priority to U.S. Provisional Application No. 61/026,396, filed on Feb. 5, 2008, each of which is incorporated herein by reference in its entirety.

TECHNICAL FIELD

The present disclosure relates in general to the field of external fixation device, and more specifically, to an external fixator ring and other external supports having a unique hole location and orientation for use as part of an external fixation system.

BACKGROUND

Without limiting the scope of the present disclosure, its background is described in connection with external fixation devices. Generally, external fixation devices are commonly used on both the upper and lower limbs for both adults and children in a variety of surgical procedures including limb lengthening, deformity correction and treatment of fractures, mal-unions, non-unions and bone defects.

One common external fixation device is known as the Ilizarov Apparatus. The Ilizarov external fixation procedure involves a rigid framework consisting of several rings or arches that are placed externally around the limb and attached to injured (e.g., due to fracture) or surgically separated (e.g., for limb lengthening and deformity correction) bone segments using special bone fasteners (wires and pins) inserted into the bone segment and connected to the related section of the external rigid framework. The opposite rings of the rigid framework are connected by either threaded or telescopic connection rods or by assembled uni-planar or multi-planar angular hinges, which allow the surgeon to adjust the relative position of the rings to each other longitudinally or angularly over a period of time. This allows new bone to gradually form in the gap between bone segments created by this distraction technique. Once the desired position of bone segments is achieved over the course of time (e.g., 2-6 weeks), the external apparatus is stabilized into a fixed position and left on the bone segments until the fracture is healed or newly formed bone is completely or substantially mineralized, which could take up to an additional 3-6 months, depending on the nature of pathology and degree of deformity.

Another common external fixation device is a Taylor Spatial Frame as described in U.S. Pat. Nos. 6,030,386, 5,891,143, and 5,776,132. The Taylor Spatial Frame is a hexapod type of device based on a Stewart platform but shares many components and features of the Ilizarov apparatus. The Taylor Spatial Frame consists of two external fixator rings attached to bone segments by wires or half pins and connected together by 6 struts that may be lengthened or shortened as necessary. Adjustment of strut lengths allows manipulation of the bone segments in 6 axes (e.g., lengthening/shortening, external/internal rotation, anterior/posterior horizontal translation, medial/lateral horizontal translation, anterior/posterior angular translation, and medial/lateral angular translation) to correct linear, angular and rotational deformities simultaneously. The rings of the device include apertures or holes for attachment of wires and half pins and positioning of the struts and other connection elements. However, there are a finite number of holes on each ring, six of which are occupied with struts. This creates a positioning problem for wire and half pin attachment and placement of the additional connection rods due to the competition for holes in the ring.

In addition, the configuration of the rings of the Taylor Spatial Frame requires the struts to be connected at the top or bottom of the rings. To provide such connections, the rings are configured to receive only either ball joints in the holes of the rings or universal joints extending from the top or bottom surfaces of the rings. Both types of joints, however, have drawbacks. One drawback for using rings that are coupled to ball joints is that there is insufficient spatial clearance for the ball joints to effect some adjustments to the orientation of the struts and the rings. A drawback for using rings coupled to universal joints is the decrease in the functional length of the struts due to the space taken up by the length of the universal joints. Another drawback is the instability caused by universal joints. The universal joints each include at least one hinge connection, in which a pivot pin is commonly and loosely held by two rotating parts that are designed to rotate about the longitudinal axis defined by the pivoting pin. Due to the loose coupling between the rotating parts and the pivoting pin, a degree of undesirable translational movement is inherent in the design of the hinge connection and introduces instability to the Taylor Spatial Frame. Accordingly, the requirement of attaching the struts at the top or bottom of the rings ultimately leads to instability and limited range of motion in the Taylor Spatial Frame.

SUMMARY

The present disclosure provides an external fixator ring that includes a central opening, inner and outer ring surfaces and upper and lower ring surfaces, one or more apertures extending through the upper ring surface to the lower ring surface, one or more angled flanges extending radially from the outer surface, and one or more apertures that extend at least partially into the outer surface of the ring. Each of one or more angled flanges comprises one or more apertures that extend at least partially into the outer surface of the ring and is adapted to provide rigid attachment for connection struts while allowing maximal range of motion between the interconnected rings.

BRIEF DESCRIPTION OF THE DRAWINGS

For a more complete understanding of the features and advantages of the present disclosure, reference is now made to the detailed description along with the accompanying figures and in which.

DETAILED DESCRIPTION

While the making and using of various embodiments of the fixator ring according to the present disclosure are discussed in detail below, it should be appreciated that the present application provides many applicable inventive concepts that can be embodied in a wide variety of specific contexts. The specific embodiments discussed herein are merely illustrative of specific ways to make and use the fixation device disclosed herein and do not delimit the scope of the application, and their usage does not delimit the application, except as outlined in the claims.

The present application discloses a fixator ring fabricated from a suitably strong and rigid material such as a metal, alloy, plastic, composite, or ceramic. The body portion of the ring includes substantially equally spaced apertures or holes positioned arcuately therein and extending through the upper ring surface to the lower ring surface, substantially equally spaced angled flanges extending radially from the outer surface of the ring and substantially equally spaced apertures that extend at least partially into the outer surface of the ring. During an operation, the arcuately positioned holes are used to connect wires and half pins inserted to the bone segments while angled flanges and apertures are used for attachment of connection struts. The apertures are positioned obliquely in the angled flange to provide the optimal range of motion for the strut when connected to the fixator ring. In addition, struts can be connected to other apertures on outer or inner surfaces of the ring.

Figure 1:
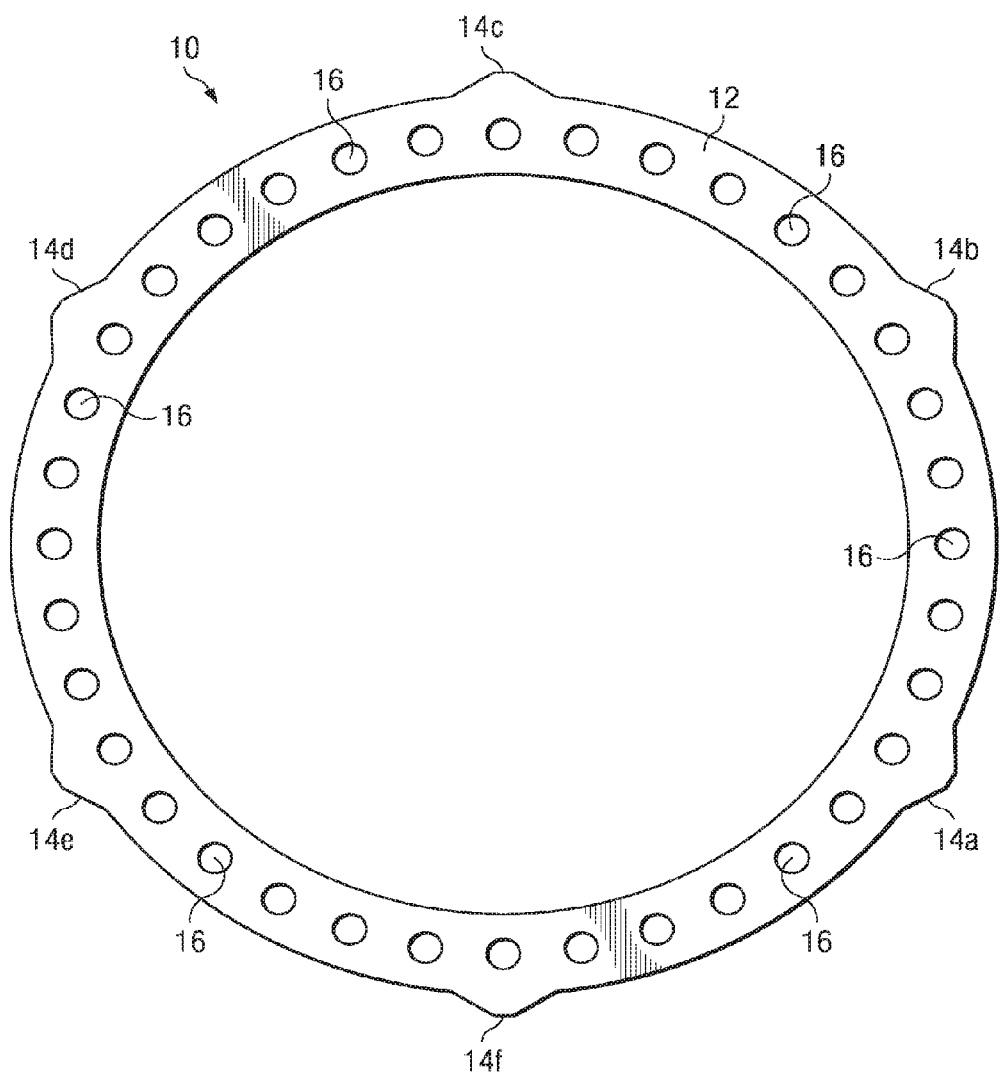
FIG. 1 is a top view of a fixator ring according to one embodiment of the present disclosure.

FIG. 1 is a top view of the fixator ring 10 of the present application. The fixator ring 10 includes a top surface 12, a bottom surface (not shown), an inner side surface (not shown) and an outer side surface (not shown). The fixator ring 10 has numerous angled flanges 14a, 14b, 14c, 14d, 14e and 14f extending from the outer side surface (not shown) to provide mounting surfaces for connection struts. The fixator angled flanges 14 may be placed at various positions on the fixator ring 10. The top surface 12 includes numerous top holes 16 that extend through the top surface 12 to the bottom surface (not shown). The top holes 16 may be used for attachment of wire and half pin fixation elements (bolts), threaded or telescopic connection rods, plates, posts or other device connection elements for connecting to the ring 10.

Figure 2A:
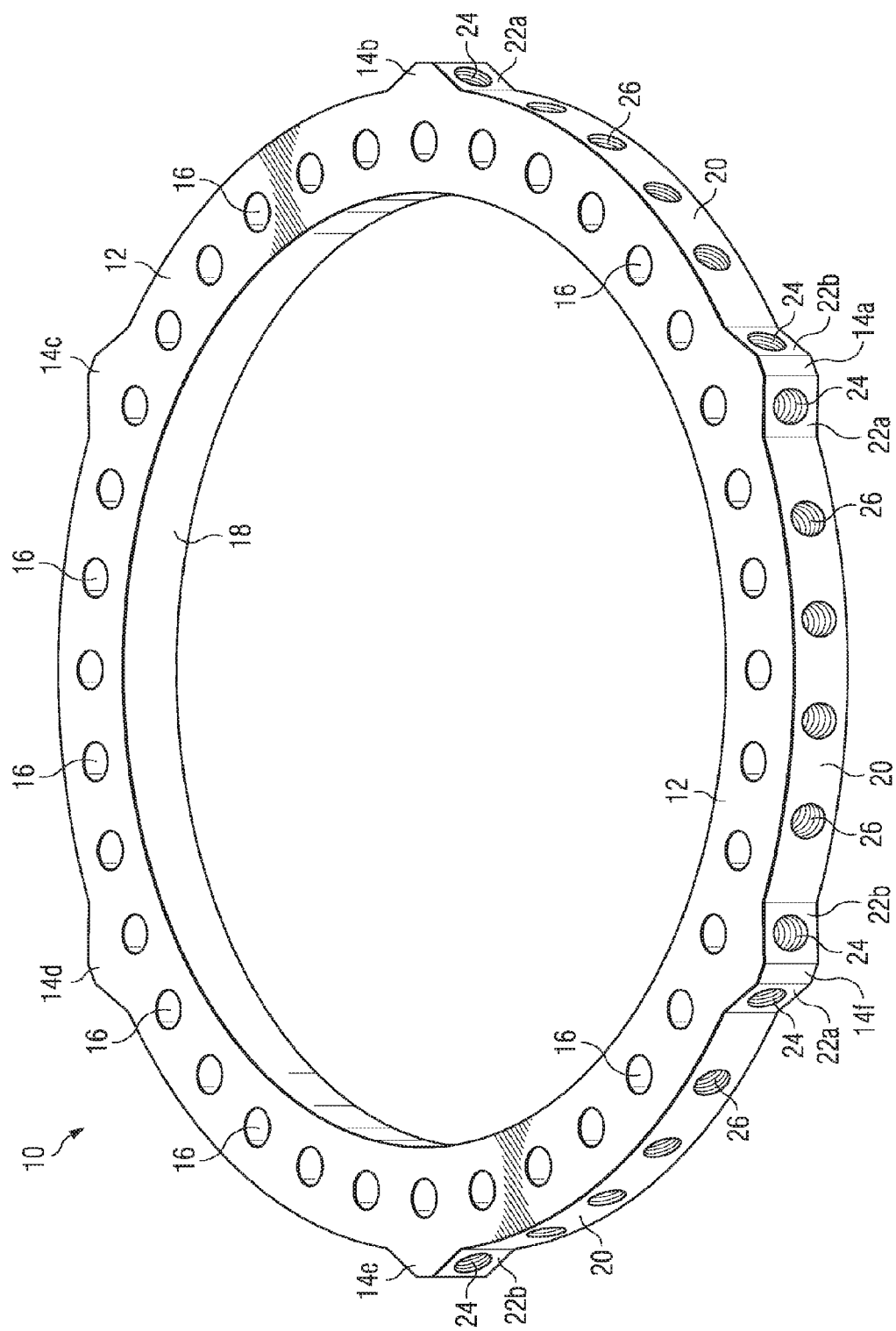
FIG. 2A is a perspective view of one embodiment of the fixator ring of FIG. 1.
Figure 2B:
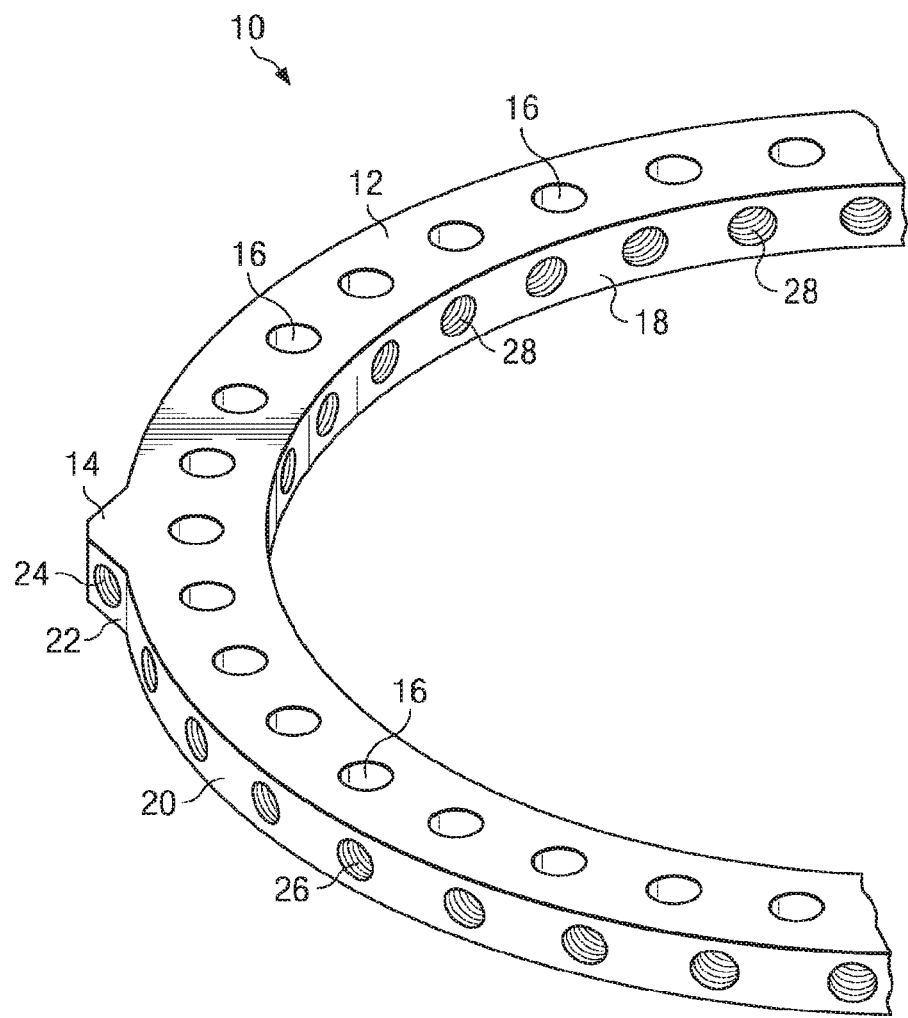
FIG. 2B is a perspective view of a portion of the embodiment of the fixator ring shown in FIG. 2A.

Referring to the embodiments shown in FIGS. 2A and 2B, the fixator ring 10 includes a top surface 12, a bottom surface (not shown), an inner side surface 18 and an outer side surface 20. The top surface 12 includes numerous top holes 16 that extend through the top surface 12 to the bottom surface (not shown). The top holes 16 may be used for attachment of wire and half pin fixation elements (bolts), threaded or telescopic connection rods, plates, posts or other device connection elements to the ring 10. The fixator ring 10 has angled flanges 14 extending from the outer side surface 20 to provide mounting surfaces 22a and 22b for connection struts. Each mounting surface 22a and 22b of the angled flanges 14 includes a threaded aperture 24 that extends into the outer surface 20 of the ring 10 and is adapted to provide attachment for connection struts (not shown). The outer side surface 20 includes numerous threaded apertures 26 that provide additional attachments for the struts or other connection elements. In the embodiment shown in FIG. 2B, the inner side surface 18 includes threaded apertures 28 for receiving the struts or other connections element. It is to be appreciated that in some embodiments, the fixator ring 10 may include flanges 14 but not apertures 24 or 28. In some other embodiments, the fixator ring 10 may include apertures 24 or 28 but not flanges 14.

Although not shown in FIG. 2A or 2B, it is to be appreciated that an information indicator may be mounted onto or embedded into the fixator ring 10 or disposed proximate to the flanges 14. In some embodiments, the information indicator may be in the form of a code, color, or serial number corresponding to relevant information. Examples of the relevant information embodied or represented by the information indicator may include the type of the external support, the size of the ring, flange identification information, etc. In some embodiments, the information indicator may be in the form of a bar code, magnetic strip, or radio frequency identifier that could be read by a reading device to retrieve the relevant information. In other embodiments, the information indicator may be any other device suitable to embody or represent information or a combination of the types of indicators discussed in the present application.

The number of threaded outer apertures 26 and threaded inner apertures 28 may vary depending on the size of the ring as well as the number of threaded outer apertures 26 in the angled flanges 14. In addition, the outer apertures 26, inner apertures 28 and angled flange aperture 24 may be configured to accept other connection elements of the external fixator frame 10.

The angled flanges 14 may be placed at various positions on the outer surface 20 of the fixator ring 10. Generally, the angled flanges 14 are placed at a geometric position about the fixator ring 10. For example, the fixator ring 10 may include one ore more angled flanges 14 positioned equidistant from each other about the fixator ring 10; however the distances need not be equidistant and may be of any convenient distance or spacing. The angled flanges 14 may be integrally connected or releasably coupled to the fixator ring 10. Detachable angled flanges 14 may be particularly advantageous in some embodiments because they allow for more flexibility in the placement of struts. For example, fixator systems for foot support may require additional struts to provide firmer support or to accommodate various shapes of the ring. The angled flanges 14 may be of different shapes and different sizes to provide different ranges of motion for the struts connected to the flanges 14. For example, other shapes of the angled flanges 14 include rounded flanges polygonal flanges, triangular flanges, or square flanges, when viewed from the top surface 12. In the exemplary embodiment shown in FIG. 1, the flanges 14 are angled at 120 degrees to allow the connecting struts to have a maximum range of motion. The term "angled" as used in the present disclosure refers to the angular orientation of a first mounting surface relative to a second mounting surface.

Figure 3A:
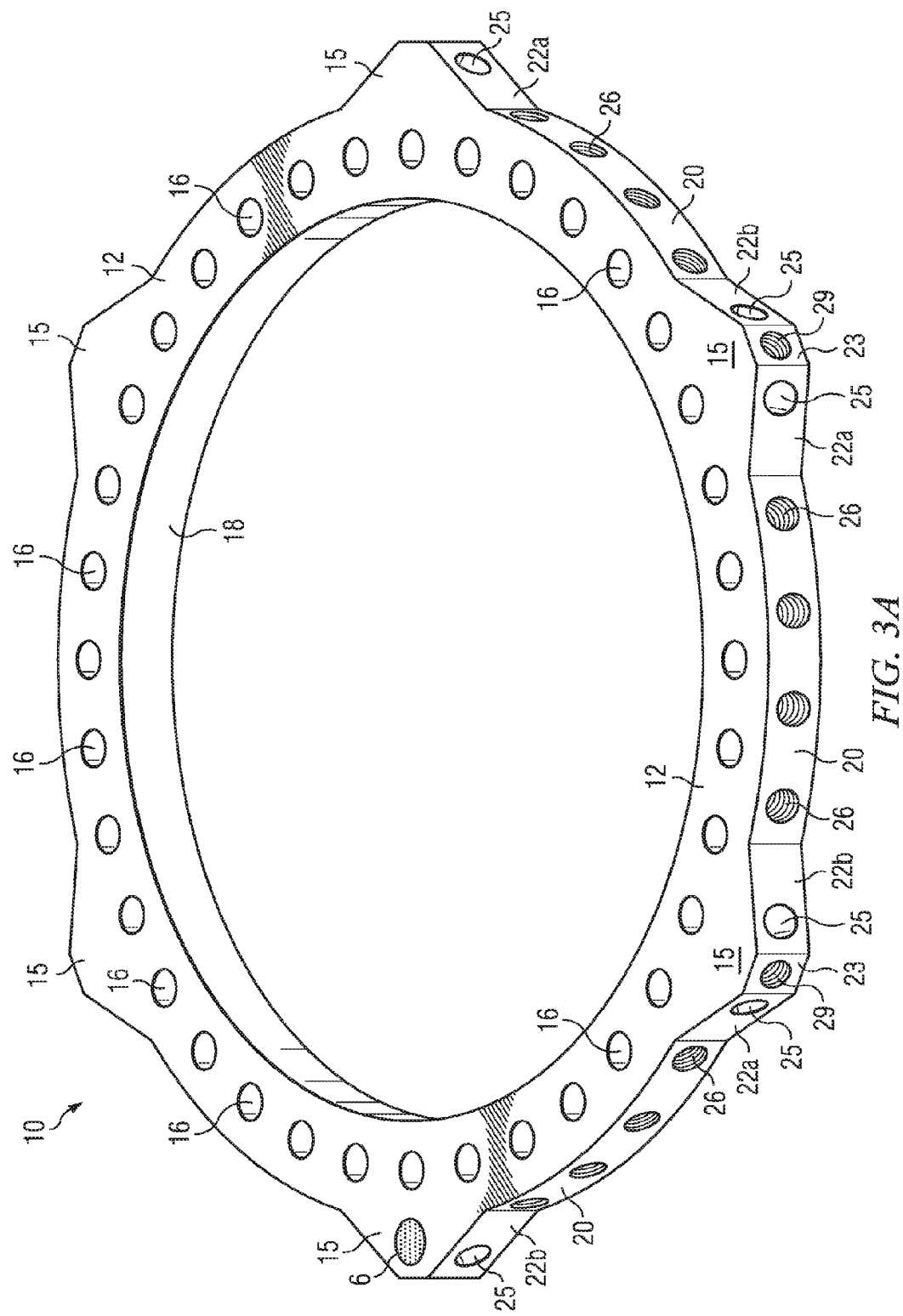
FIG. 3A is a perspective view of another embodiment of the fixator ring according to the present disclosure.
Figure 3B:
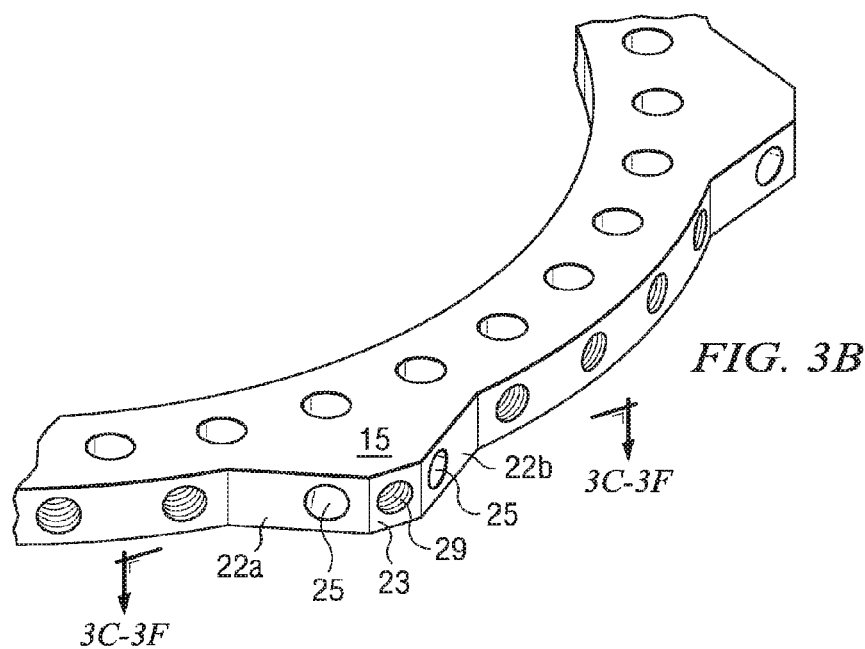
FIG. 3B is a perspective view of a portion of the embodiment of the fixator ring of FIG. 3A.

Referring to the embodiment shown in FIGS. 3A and 3B, the illustrated fixator ring 10 includes a top surface 12, a bottom surface (not shown), an inner side surface 18 and an outer side surface 20. The fixator ring 10 further has trapezoidal flanges 15 extending from the outer side surface 20 to provide mounting surfaces 22a and 22b for connection struts. Each mounting surface 22a and 22b of the trapezoidal flanges 15 includes an aperture 25 defined therein and may include an indicator 6. The apertures 25 each have a smooth (rather than threaded) inner surface and are adapted to receive studs 27 (shown in FIGS. 3C TO 3G) to provide attachment for connection struts (not shown). The trapezoidal flanges 15 each also have a securing surface 23 disposed between the mounting surfaces 22a and 22b. The securing surface 23 has an aperture 29 defined therein, and the aperture 29 is operable to receive a screw 31 (shown in FIG. 3C) for locking the studs 27 in place. In the embodiment shown in FIG. 3C, the screw 31 is a set screw.

Figure 3C:
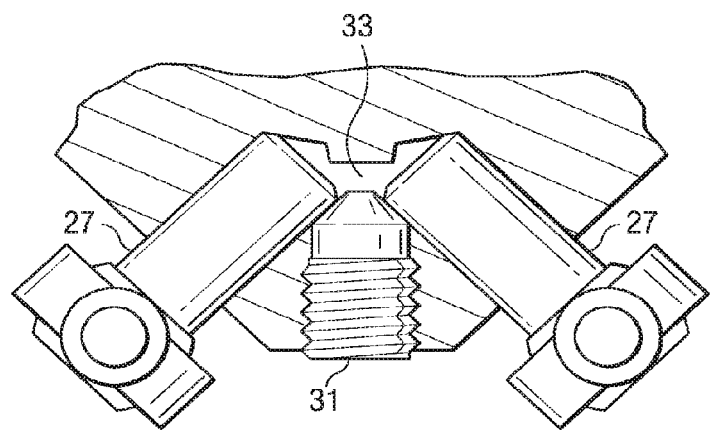
FIG. 3C is a partial sectional view of a first embodiment of a flange shown in FIG. 3B.

FIG. 3C is a partial sectional view of the fixator ring 10 of FIG. 3B when viewed from the top in the direction indicated by arrows 7. The apertures 25 and 29 meet at a recess 33 within the flange 15, which provides room for the studs 27 and set screw 31 to engage with one another inside the flange 15. The studs 27 each have an end portion that is exposed in the recess 33 when the studs 27 are received in the apertures 25 as shown in FIG. 3C. To substantially lock the studs 27 in place, the set screw 31 is inserted into the aperture 29 to engage the end portions of studs 27. The apertures 25 are aligned at an angle that substantially corresponds to the shape of the angled tip of the set screw 31, thereby increasing the contact area between the studs 27 and the set screw 31.

It is to be appreciated that the number and orientation of the apertures 25 and 29 can vary in some embodiments to accommodate various design needs. For example, in some exemplary embodiments, the alignment of the apertures 25 can be altered to accommodate different sizes and configurations of the set screw 31 and/or studs 27. It is to be further appreciated that dynamic loading on the contact surface between the studs 27 and the set screw 31 can cause the contact surface to deform and ultimately cause the studs 27 to become loosened. Thus, the apertures 25 and 29 can be configured to receive studs 27 having grooves defined therein to allow for optimal gripping and to accommodate for the dynamic loading of the contact surface.

Figure 3D:
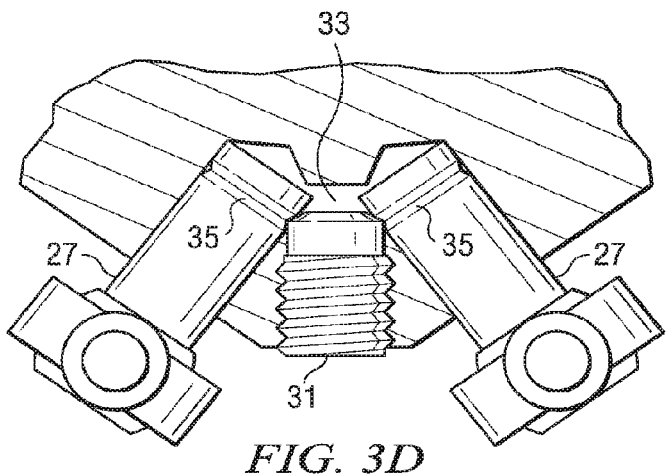
FIG. 3D is a partial sectional view of a second embodiment of a flange shown in FIG. 3B.

FIG. 3D is a partial sectional view of an exemplary embodiment of the flange 15 of FIG. 3B. In this embodiment, the flange 15 is configured to receive studs 27 having grooves 35 defined therein. The grooves 35 are defined in the end portions of the studs 27, such that, when the studs 27 are received in the apertures 25, grooves 35 are exposed in the recess 33 as shown in FIG. 3D. The studs 27 are aligned at an angle that allows the set screw 31 to be inserted into the aperture 29 and engage the grooves 35 of both studs 27, thereby substantially locking the studs 27 in place.

Figure 3E:
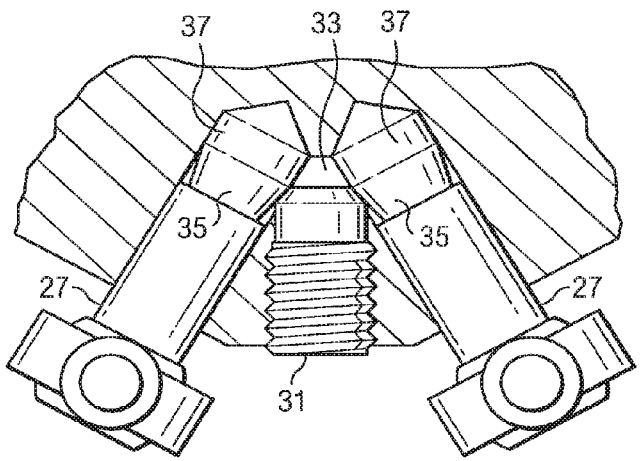
FIG. 3E is a partial sectional view of a third embodiment of a flange shown in FIG. 3B.

Shown in FIG. 3E is another exemplary embodiment of the flange 15 of FIG. 3B. The stud 27 includes a conical tip 37 and grooves 35 defined therein. The conical tip 37 allows for better guidance for the insertion of the stud 27 and increased contact surface between the stud 27 and the walls of the recess 33 for improved stability. In addition, the inclusion of a conical tip 37 increases the effective length of the stud 27 and further improves the stability of the stud 27 in aperture 25.

Figure 3F:
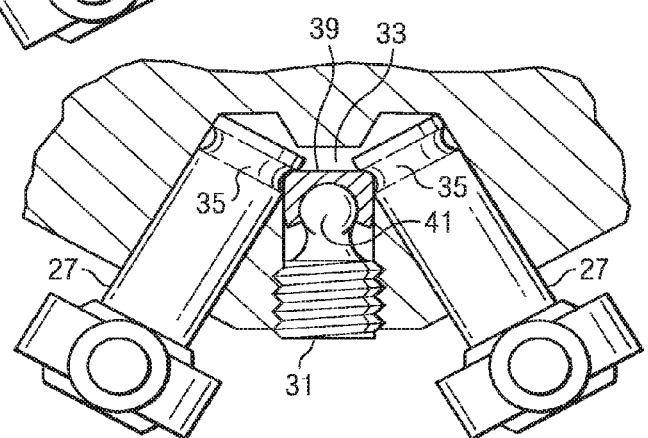
FIG. 3F is a partial sectional view of a fourth embodiment of a flange shown in FIG. 3B.

FIG. 3F is a partial sectional view of another exemplary embodiment of the flange 15 of FIG. 3B. The illustrated set screw 31 includes an engagement portion 39 pivotally mounted onto tip 41, and the engagement portion 39 is operable to swivel until it is securely fit into the grooves 35 of both studs 27. The engagement portion 39 allows the binding load on the studs 27 to be distributed more equally between the studs 27.

Figure 3G:
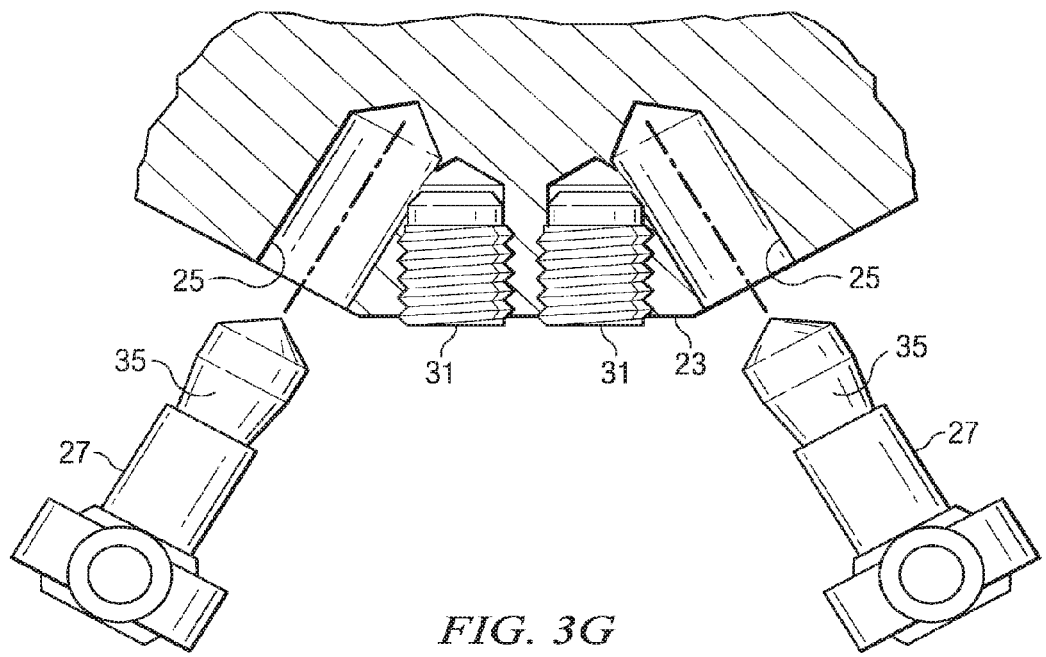
FIG. 3G is a partial sectional view of a fifth embodiment of a flange shown in FIG. 3B.

FIG. 3G a partial sectional view of yet another exemplary embodiment of the flange 15 of FIG. 3B. The securing surface 23 of the flange 15 includes two apertures 29 defined therein, each operable to receive a set screw 31 for substantially locking one of the two studs 27. As a result, the studs 27 can be independently locked by a different set screw 31.

Figure 4:
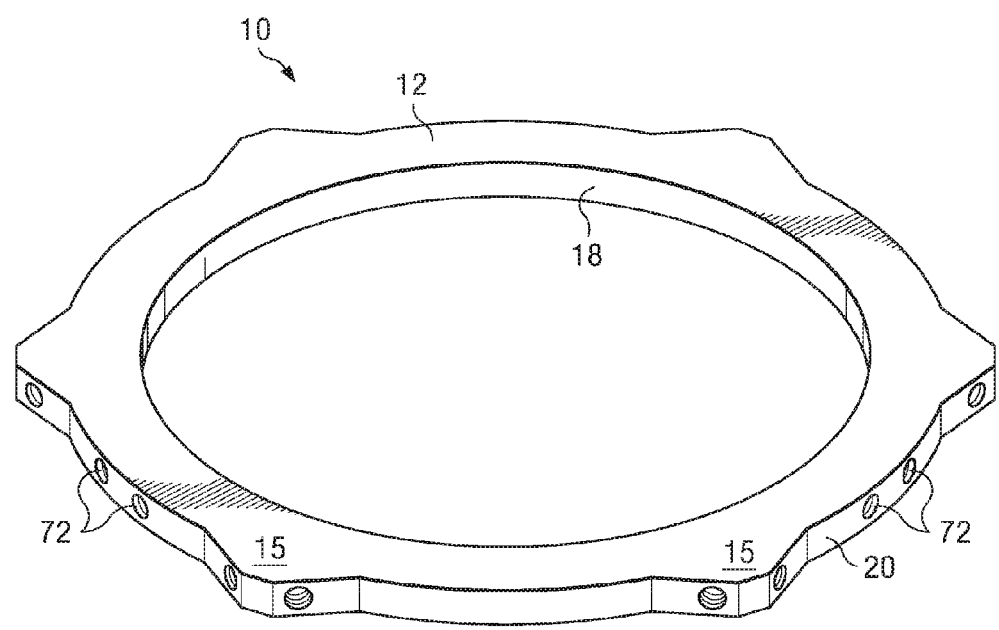
FIG. 4 is a perspective view of yet another embodiment of the fixator ring according to the present disclosure.

FIG. 4 is a perspective view of a fixator ring 10 that is operable to receive a positional marker 70 (shown in FIG. 5). A positional marker 70 can be any markers used in orthopedic applications, such as a radiological marker used to determine the spatial orientation of the fixator ring 10. The fixator ring 10 includes a top surface 12, a bottom surface (not shown), an inner side surface 18 and an outer side surface 20. The fixator ring 10 further has trapezoidal flanges 15 as described above with reference to FIGS. 3A to 3G. Furthermore, the fixator ring 10 includes at least a pair of recessed portions 72 defined therein for receiving the nodules 74 of the marker 70 and substantially securing the marker 70 in one orientation. The number and placement of the pair of recessed portions 72 can vary in different embodiments. In the exemplary embodiment showing in FIG. 4, there are four pairs of recessed portions 72 defined in the outer side surface 20 of the fixator ring 10 and spaced apart at different distances. In some embodiments, the pairs of recessed portions 72 can be equally spaced. In some other embodiments, pairs of recessed portions 72 may be defined in the inner side surface 18, the top surface 12, or the bottom surface (not shown).

Figure 5A:
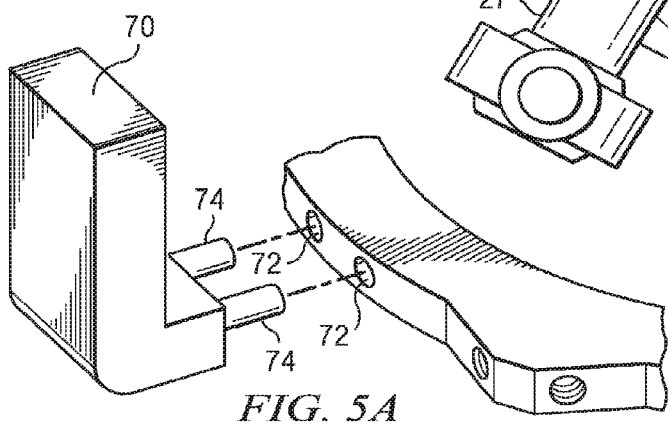
FIG. 5A is an exploded view of the fixator ring shown in FIG. 4 being coupled to a marker with a pair of round nodules.
Figure 5B:
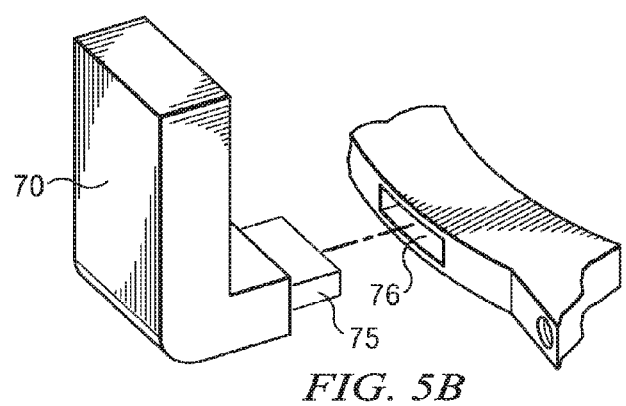
FIG. 5B is an exploded view of the fixator ring shown in FIG. 4 being coupled to a marker with a rectangular nodule.

As shown in FIG. 5A, the marker 70 has a pair of nodules 74 that would fit tightly into the recessed portions 72, which provides two points of attachment. As shown in FIG. 5A, the nodules 74 and the recessed portions 72 are round. This allows for a substantially secure coupling of the marker 70 to the fixator ring 10 because having two points of attachment prevents the marker 70 from experiencing rotational movements. It is to be appreciated that other suitable securing mechanisms can be used for securing the marker 70 to the fixator ring 10. For example, as shown in FIG. 5B, the marker 70 could be modified to include a rectangular peg 75 instead of a pair of nodules 74, and in such cases, a corresponding rectangular recessed portion 76 defined in the fixator ring 10 instead of a pair of recessed portions 72 would be sufficient to prevent rotational movements of the marker 70.

Figure 6:
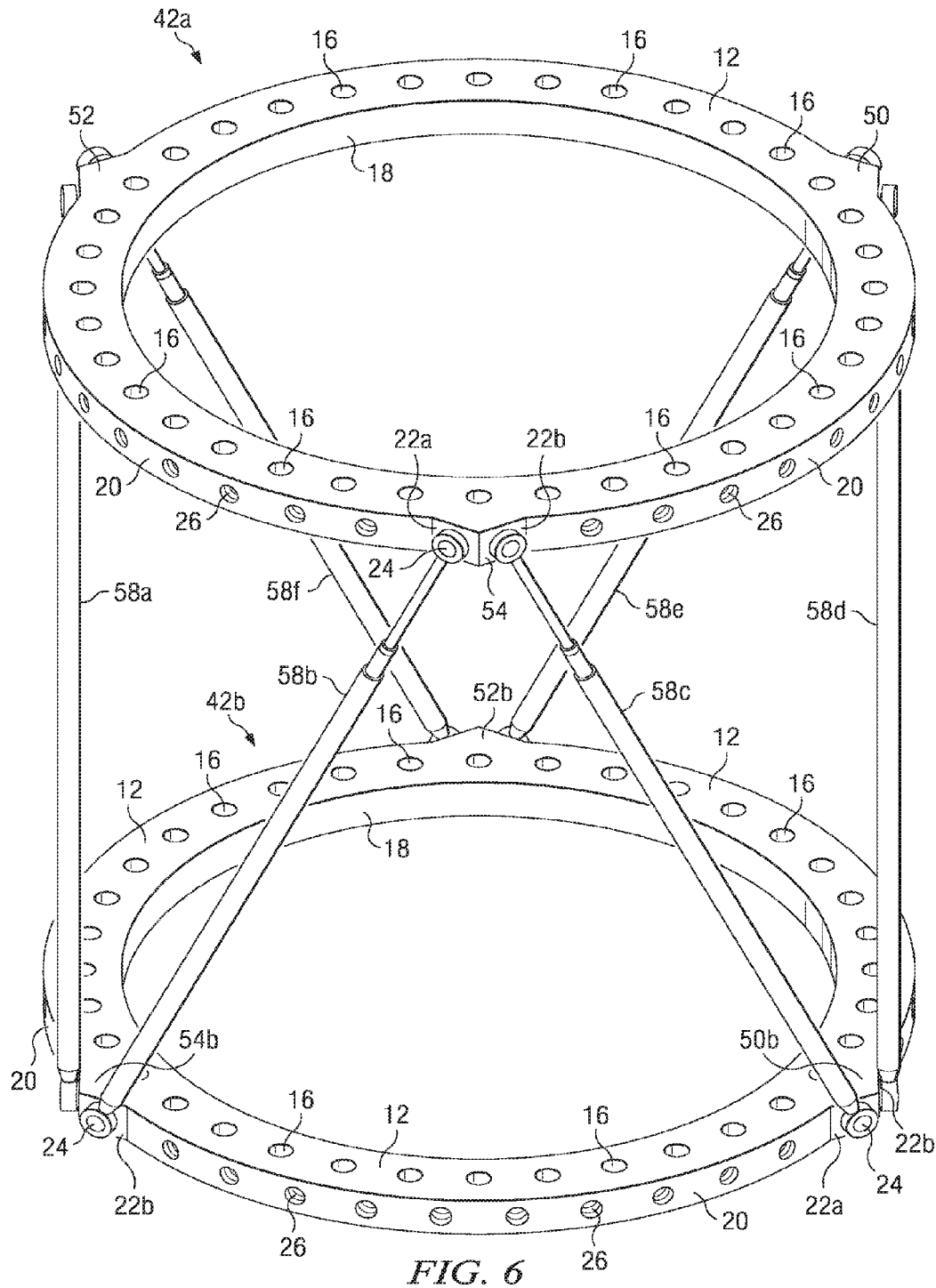
FIG. 6 is a perspective view of a fixator ring system.

FIG. 6 is a perspective view of an external fixator ring system 40. The fixator ring 42a includes a top surface 12, a bottom surface (not shown), an inner side surface 18 and an outer side surface 20. The fixator ring 42a has angled flanges 50, 52 and 54 extending from the outer side surface 20 to provide mounting surfaces 22a and 22b for connection struts 58. The top surface 12 includes numerous top holes 16 that extend through the top surface 12 to the bottom surface (not shown). The top holes 16 may be used for attachment of wire and half pin fixation elements (bolts), threaded or telescopic connection rods, plates, posts or other device connection elements to the ring 42a. The fixator angled flanges 50, 52, and 54 also include threaded outer apertures (not shown) to provide attachment for connection struts 58a, 58b, 58c, 58d, 58e and 58f. The outer side surface 20 includes numerous threaded apertures 26 that provide additional attachments for the struts 58 or other connection elements (not shown).

The second fixator ring 42b includes a top surface 12, a bottom surface (not shown), an inner side surface 18 and an outer side surface 20. The fixator ring 42b has angled flanges 50b, 52b and 54b extending from the outer side surface 20 to provide mounting surfaces 22a and 22b for connection struts 58. The top surface 12 includes numerous top holes 16 that extend through the top surface 12 to the bottom surface (not shown). The top holes 16 may be used for attachment of wire and half pin fixation elements (bolts), threaded or telescopic connection rods, plates, posts or other device connection elements to the ring 42b. The fixator angled flanges 50, 52 and 54 also include threaded outer apertures (not shown) to provide attachment for connection struts 58a, 58b, 58c, 58d, 58e and 58f. The outer side surface 20 includes numerous threaded apertures 26 that provide additional attachments for the struts or other connection elements (not shown).

Although the shape of the fixator rings 42a and 42b as shown FIG. 6 is substantially circular, it is to be appreciated that the shape of the fixator rings 42a and 42b can vary to accommodate the physical contour of various body parts to which the fixation system 40 would be attached. For example, the fixator rings 42a and 42b can be configured to have an oval shape, D-shape, U-shape, C-shape, or other irregular shapes. In some exemplary embodiments, an elliptical fixator ring (not shown) may be particularly advantageous. The insertion of pins or wires into a patient's limb can cause the surrounding tissue to swell unevenly, and in such a case, an elliptical fixator ring can accommodate the uneven swelling better than a circular ring can. The fixator rings 42a and 42b may be a complete ring (full ring) or a segment or portion of a ring (e.g., half ring, ⅓ ring, ¼ ring, ⅜ ring, ⅝ ring, ⅔ ring, ¾ ring, and other) that is either used alone or joined with other segments or portions of the ring to form a fixator ring (not shown). The fixator rings 42a and 42b may be constructed of any material that provides the structural rigidity necessary for fixation such as metal, alloy, carbon fiber, plastic, ceramic and so forth.

Figure 7:
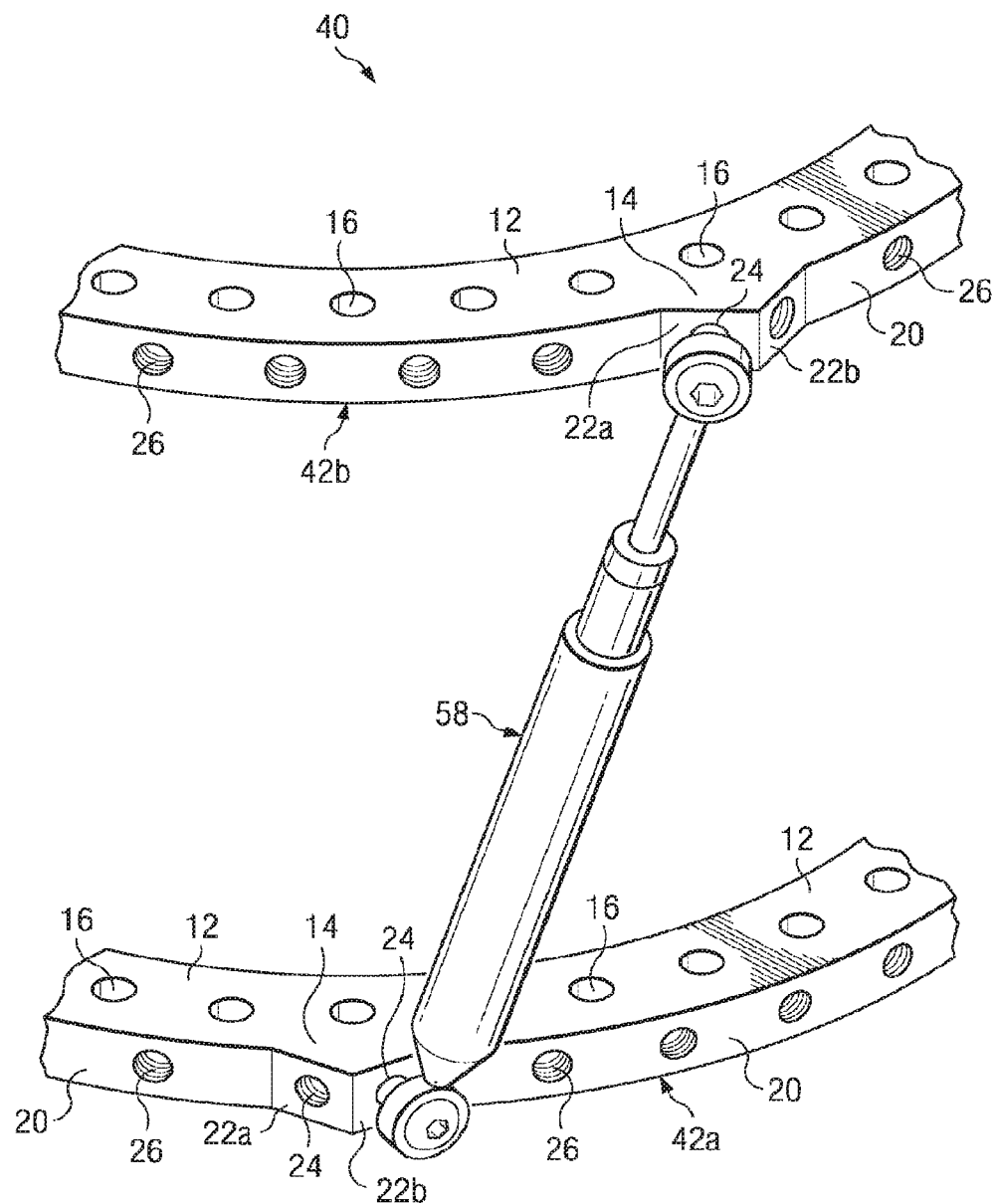
FIG. 7 is a side view of one embodiment of the fixator ring system of FIG. 6.

FIG. 7 is a side view of one embodiment of a fixator ring system 40. The fixator ring system 40 of the present application is illustrated as a portion of the specific design for simplicity. The fixator rings 42a and 42b include a top surface 12, a bottom surface (not shown), an inner side surface (not shown) and an outer side surface 20. The fixator rings 42a and 42b have an angled flanges 14 extending from the outer side surface 20 to provide mounting surfaces 22a and 22b for connection struts 58. The top surface 12 includes numerous top holes 16 that extend through the top surface 12 to the bottom surface (not shown). The top holes 16 may be used for attachment of wire and half pin fixation elements (bolts), threaded or telescopic connection rods, plates, posts or other device connection elements to the ring 42. The angled flanges 14 also include threaded outer apertures 24 to provide attachment for connection struts 58. A single connecting strut 58 connects the fixator rings 42a and 42b. The outer side surface 20 includes numerous threaded apertures 26 that provide additional attachments for the struts 58 or other connection elements (not shown).

A connecting strut 58 is disposed between the first external fixator ring 42a and the second external fixator ring 42b for the sake of simplicity. The skilled artisan will readily understand that numerous connecting rods 58 may be attached at various positions about the external fixator rings, that the angle of the connecting rod 58 relative to the first external fixator ring 42a and the second external fixator ring 42b may be varied, and that the length of the connecting rod 58 may be varied and adjusted.

In addition, the present application provides a method and apparatus for stabilization using multiple external fixator rings as a single device. For example, a first external fixator ring having 6 equidistant angled flanges is connected to a second external fixator ring having 6 equidistant angled flanges as above. A third external fixator ring is connected to the first external fixator ring, the second external fixator ring or both using the three unused angled flanges.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An external fixator ring comprising:
a ring with a central opening defined therethrough, the ring having inner and outer ring surfaces and upper and lower ring surfaces, and an outer longitudinal edge in the outer ring surface perpendicular to the upper and lower ring surfaces;
one or more apertures extending through the upper ring surface to the lower ring surface;
one or more angled flanges extending radially from said inner or outer ring surface, each angled flange comprising a first mounting surface, a second mounting surface, and a securing surface positioned between the first and second mounting surfaces;
each of said angled flanges comprising two strut connection apertures extending at least partially into the first and second mounting surfaces and having a smooth inner surface operable to receive studs providing attachment to a ring connection strut; and,
each of said angled flanges comprising a receiving aperture extending at least partially into the securing surface so as to intersect with the two strut connection apertures, said receiving aperture operable to receive a locking screw to lock the studs into the adjacent strut connection apertures.

2. The external fixator ring of claim 1, wherein the receiving strut connection apertures and the receiving aperture meet at a recess defined in the inner or outer ring surface.

3. The external fixator ring of claim 2, wherein the locking screw comprises an angled tip and the studs comprise a smooth surface at the end portion of the studs, wherein the angled tip of the locking screw can be driven into contact with the smooth surface at the end portion of the studs within the recess to lock the studs in place.

4. The external fixator ring of claim 2, wherein each of the studs comprises a groove at the end portion of the studs, wherein the tip of the locking screw can be driven into contact with the groove at the end portion of the studs within the recess to lock the studs in place.

5. The external fixator ring of claim 4, wherein two strut connection apertures meet with one receiving aperture within the recess so that one locking screw can lock two studs in place.

6. The external fixator ring of claim 2, further comprising:
each of the strut connection apertures comprising a conical recess at the end of the apertures,
each of the studs comprising a conical tip and a conical groove at the end portion of the studs,
each of the locking screws comprising a beveled edge at the end of the locking screws,
wherein the conical tip of the studs is operable to be driven into contact with the conical recess at the end of the strut connection aperture,
and wherein the beveled edge at the end of the locking screw can be driven into contact with the conical groove at the end portion of the studs within the recess to lock the studs in place.

7. The external fixator ring of claim 6, wherein two strut connection apertures meet with one receiving aperture within the recess so that one locking screw can lock two studs in place.

8. The external fixator ring of claim 2, further comprising:
each of the studs comprising a groove at an end portion of the stud,
each of the locking screws comprising a pivotally attached engagement portion at the tip of the locking screw,
wherein the engagement portion of the locking screw can be driven into contact with the groove at the end portion of the studs within the recess to lock the studs in place.

9. The external fixator ring of claim 8, wherein two strut connection apertures meet with one receiving aperture within the recess so that the engagement portion of the locking screw is operable to swivel until it securely fits within the grooves of the studs so as to lock the studs in place.

10. The external fixator ring of claim 9, wherein the tip of the locking screw comprises a ball and the engagement portion comprises a recess operable to be pivotally mounted to the ball.

11. The external fixator ring of claim 10, wherein two strut connection apertures meet with one receiving aperture within the recess so that one locking screw locks two studs in place.

12. The external fixator ring of claim 1, wherein the one or more angled flanges comprise trapezoidal flanges.

13. The external fixator ring of claim 1, wherein:
the locking screw further comprises an angled tip; and
the strut connection aperture and the receiving aperture are aligned at an angle that substantially corresponds to the shape of the angled tip of the locking screw.

14. The external fixator ring of claim 13, wherein the locking screw comprises a set screw configured for engaging the end portion of one or more studs.

15. An external fixator ring comprising:
a ring with a central opening defined therethrough, the ring having inner and outer ring surfaces and upper and lower ring surfaces;
one or more apertures extending through the upper ring surface to the lower ring surface;
one or more angled flanges extending radially from said outer ring surface, each angled flange comprising a first mounting surface, a second mounting surface, and a securing surface forming a trapezoidal shape;
each angled flange comprising two strut connection apertures extending at least partially into the first and second mounting surfaces, each of the strut connection apertures having a smooth inner surface operable to receive a stud providing attachment to a ring connection strut;
each angled flange further comprising a receiving aperture extending at least partially into the securing surface so as to intersect with the two strut connection apertures, said receiving aperture operable to receive a locking screw to lock the studs into the adjacent strut connection apertures; and
wherein the strut connection apertures and the receiving aperture meet at a recess within the ring.

16. The external fixator ring of claim 15, wherein the locking screws comprise an angled tip and the studs comprise a smooth surface at the end portion of the studs, wherein the angled tip of the locking screw can be driven into contact with the smooth surface at the end portion of the studs within the recess to lock the studs in place.

17. The external fixator ring of claim 16, wherein two strut connection apertures meet with one receiving aperture within the recess so that one locking screw can lock two studs in place.

18. The external fixator ring of claim 17, wherein each of the studs comprise a groove at the end portion of the stud, wherein the tip of the locking screw can be driven into contact with the groove at the end portion of the stud within the recess to lock the studs in place.

19. The external fixator ring of claim 16, wherein two strut connection apertures meet with one receiving aperture within the recess so that one locking screw can lock two studs in place.

20. The external fixator ring of claim 15, further comprising:
   each of the strut connection apertures comprising a conical recess at the end of the apertures;
   each of the studs comprising a conical tip and a conical groove at an end portion of the stud;
   each of the locking screws comprising a beveled edge at the end of the locking screws;
   wherein the conical tip of the studs is operable to be driven into contact with the conical recess at the end of the strut connection aperture; and
   wherein the beveled edge of the locking screw can be driven into contact with the conical groove at the end portion of the studs within the recess to lock the studs in place.

21. The external fixator ring of claim 20, wherein two strut connection apertures meet with one receiving aperture within the recess so that one locking screw can lock two studs in place.

22. The external fixator ring of claim 21, wherein each strut connection aperture meets with a corresponding receiving aperture within the recess so that one locking screw locks one only stud in place.

23. The external fixator ring of claim 15, further comprising:
   each of the studs comprising a groove at the end portion of each of the studs,
   each locking screw comprising a pivotally attached engagement portion at the tip of the locking screw,
   wherein the engagement portion of locking screw can be driven into contact with the groove at the end portion of the studs within the recess to lock the one or more studs in place.

24. The external fixator ring of claim 23, wherein two strut connection apertures meet with one receiving aperture within the recess so that the engagement portion of the locking screw is operable to swivel until it securely fits within the grooves of the studs so as to lock the two studs in place.

25. The external fixator ring of claim 23, wherein the tip of the locking screw comprises a ball and the engagement portion comprises a recess operable to be pivotally mounted to the ball.

26. The external fixator ring of claim 23, wherein two strut connection apertures meet with one receiving aperture within the recess so that one locking screw can lock two studs in place.

* * * * *